United States Patent
Bromberg et al.

(10) Patent No.: US 9,711,254 B2
(45) Date of Patent: Jul. 18, 2017

(54) TOROIDAL BENDING MAGNETS FOR HADRON THERAPY GANTRIES

(71) Applicant: Massachusetts Institute Of Technology, Cambridge, MA (US)

(72) Inventors: Leslie Bromberg, Sharon, MA (US); Philip C. Michael, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/051,792

(22) Filed: Feb. 24, 2016

(65) Prior Publication Data

US 2016/0247591 A1    Aug. 25, 2016

Related U.S. Application Data

(60) Provisional application No. 62/119,870, filed on Feb. 24, 2015.

(51) Int. Cl.
| | |
|---|---|
| H01J 3/14 | (2006.01) |
| G21K 1/093 | (2006.01) |
| A61N 5/10 | (2006.01) |

(52) U.S. Cl.
CPC ........... *G21K 1/093* (2013.01); *A61N 5/1077* (2013.01); *A61N 2005/1087* (2013.01); *A61N 2005/1092* (2013.01)

(58) Field of Classification Search
CPC ........... G21K 5/00; G21K 5/04; A61N 5/1077
USPC ....................... 250/396 R, 396 ML
See application file for complete search history.

(56) References Cited

U.S. PATENT DOCUMENTS

| | | | | |
|---|---|---|---|---|
| 4,251,728 | A * | 2/1981 | Pfeiffer | H01J 37/1475 250/396 ML |
| 2003/0025085 | A1 * | 2/2003 | Nakano | B82Y 10/00 250/396 ML |
| 2005/0139787 | A1 * | 6/2005 | Chiba | A61N 5/10 250/492.3 |
| 2006/0049902 | A1 | 3/2006 | Kaufman | |
| 2010/0013418 | A1 | 1/2010 | Kruip et al. | |
| 2013/0001432 | A1 * | 1/2013 | Jongen | A61N 5/10 250/396 R |
| 2016/0213951 | A1 * | 7/2016 | Uhlemann | A61N 5/1049 |

FOREIGN PATENT DOCUMENTS

| | | |
|---|---|---|
| GB | 315016 A | 7/1929 |
| JP | 2000-197263 A | 7/2000 |
| JP | 2005-310887 A | 11/2005 |

OTHER PUBLICATIONS

International Search Report and Written Opinion mailed May 23, 2016 in corresponding PCT application No. PCT/US2016/019267.

* cited by examiner

*Primary Examiner* — Jason McCormack
(74) *Attorney, Agent, or Firm* — Nields, Lemack & Frame, LLC

(57) ABSTRACT

Toroidal superconducting magnets can be used as light-weight rotating bending magnets in hadron therapy gantries. The toroidal bending magnets are self-shielded and do not require ferromagnetic material for field modification or shielding, decreasing both the magnet system weight, as well as overall gantry weight. Achromatic magnet can be made by combining two of these bending magnets. The simple geometry may allow the use of higher fields, making it attractive for carbon, as well as proton.

15 Claims, 16 Drawing Sheets

TOROIDAL BENDING MAGNETS FOR HADRON THERAPY GANTRIES

This application claims priority of U.S. Provisional Patent Application Ser. No. 62/119,870, filed Feb. 24, 2015, the disclosure of which is incorporated herein by reference in its entirety.

BACKGROUND

Several gantry designs for proton and carbon beam therapy exist and are commercially provided by multiple manufacturers. The existing designs are all based upon dipole-type bending magnets. Because of the stray magnetic field, either a large amount of external ferromagnetic shielding is required (such as iron), or a second set of coils with reversed field are needed to reduce or eliminate the fringe magnetic field from the dipole. In either case, the weight of the magnets is high. Means to reduce the weight and size of the system are desirable. In addition, some modalities of particle beam therapy require beam scanning. The goal is for the Bragg peak to be scanned in all three dimensions: ordinate and coordinate (within the treatment plane at fixed beam energy) and in depth (varying the location of the treatment plane within the body). Depth variation requires the ability to vary the energy of the beam. Magnets that can compensate for the varying beam energy are being investigated. One solution that has been proposed is achromatic magnets. These magnets have two conventional dipoles separated by one or more quadrupole (focusing) magnets. The quadrupole magnets compensate for dispersion and shift in beam direction because of the variation in beam energy. The variation in beam energy is limited before the amplitude of the magnetic field needs to be adjusted.

In addition, because of the desire to be able to scan the beam, a large aperture is required, at least for the final bending magnet. The scanning beam may be upstream from the last bending magnet. To prevent interception the beam, the aperture at the exit of the last bending magnet needs to be fairly large.

The use of toroidal magnets for beam physics application is well known. In particular, one of the largest, most powerful bending magnets, the ATLAS Barrel Torus, is a toroidal magnet. In the ATLAS magnet design, the magnetic field actually has substantial radial variation and has relatively low aspect ratio, unfavorably affecting the optics of the beam. Large coil aspect ratio is desirable, as will be described below, to minimize the size and weight of the toroidal bending magnet. The toroidal magnet has the advantage that there is no need, or minimal need, for magnetic shielding. Thus, the iron required in the case of simple dipoles, or the second coil needed to cancel the far fields, is not needed, substantially decreasing the weight of the system. However, this type of bending magnets has not been considered in hadron beam therapies.

It would be beneficial if toroidal magnets could be modified for use with hadron beam therapies.

SUMMARY

Toroidal superconducting magnets can be used as lightweight rotating bending magnets in hadron therapy gantries. The toroidal bending magnets are self-shielded and do not require ferromagnetic material for field modification or shielding, decreasing both the magnet system weight, as well as overall gantry weight. Achromatic magnet can be made by combining two of these bending magnets. The simple geometry may allow the use of higher fields, making it attractive for carbon, as well as protons.

According to one embodiment, a system for hadron therapies is disclosed. The system comprises a toroidal magnet, having a major axis passing through its center; a plurality of plates extending outward from the major axis, wherein each plate comprises a pancake coil disposed adjacent to a flat supporting element, wherein the pancake coil is configured so as to form a field-building region, a constant field region and a return current region; and a plurality of gaps, each gap disposed between a respective pair of adjacent plates; and a beam of charged particles directed toward one of the plurality of gaps in the toroidal magnet, wherein a path of the beam is planar with the major axis and the path forms an angle with the major axis which is greater than 0°.

According to a second embodiment, a system for hadron therapies is disclosed. The system comprises a first toroidal magnet, having a first major axis passing through its center; a plurality of first plates extending outward from the first major axis, wherein each first plate comprises a pancake coil disposed adjacent to a flat supporting element; and a plurality of first gaps, each first gap disposed between a respective pair of adjacent first plates; a second toroidal magnet, having a second major axis passing through its center; a plurality of second plates extending outward from the second major axis, wherein each second plate comprises a pancake coil disposed adjacent to a flat supporting element; and a plurality of second gaps, each second gap disposed between a respective pair of adjacent second plates; and a beam of charged particles directed toward one of the plurality of first gaps in the first toroidal magnet, wherein a path of the beam is planar with the first major axis and the path forms a first entry angle with the first major axis and exits the first toroidal magnet at a first exit angle relative to the first major axis; and wherein the second toroidal magnet is configured such that the beam, after exiting the first toroidal magnet, is directed toward one of the second gaps at a second entry angle relative to the second major axis that is equal to the first exit angle from the first toroidal magnet.

BRIEF DESCRIPTION OF THE FIGURES

For a better understanding of the present disclosure, reference is made to the accompanying drawings, which are incorporated herein by reference and in which:

FIG. 10A is an isometric view and FIG. 10B is an elevation view;

FIG. 11a is an isometric view and FIG. 11b is a view perpendicular to the average plane (the zx plane) of the beam;

FIG. 16A shows the desired direction of the current of the quadrupole magnet and FIG. 16B shows one implementation of a modification of the turns in the plate to achieve the desired quadrupole currents;

DETAILED DESCRIPTION

Figure 1A:
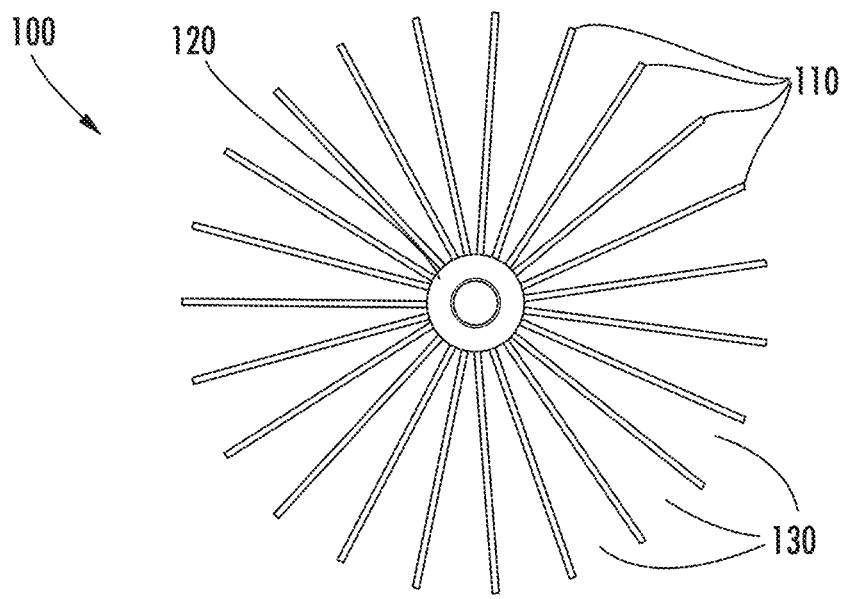
FIG. 1A is a top view of a toroidal bending magnet for hadron therapy.
Figure 1B:
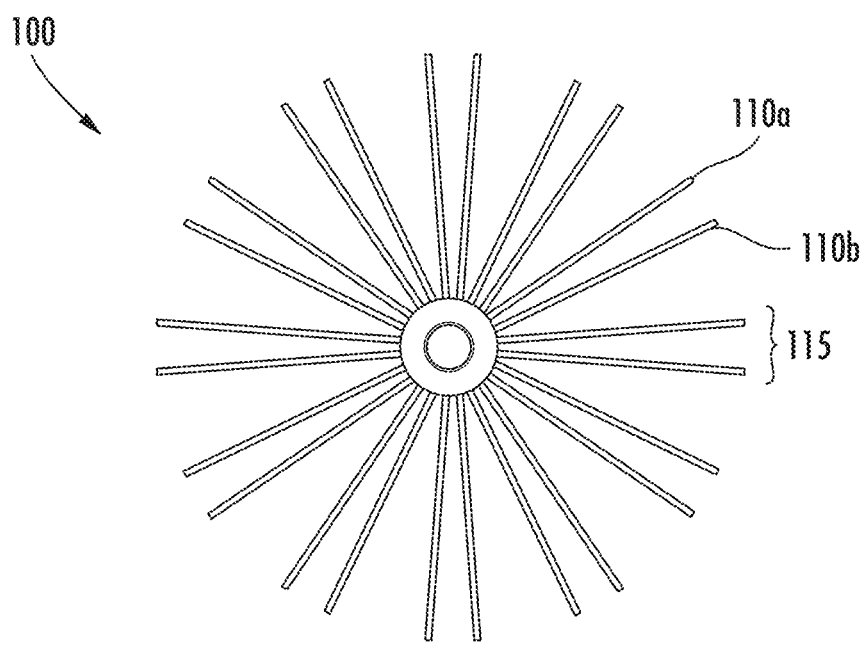
FIG. 1B is a magnet similar to that shown in FIG. 1a, but with plates arranged non-uniformly distributed around the torus.
Figure 1C:
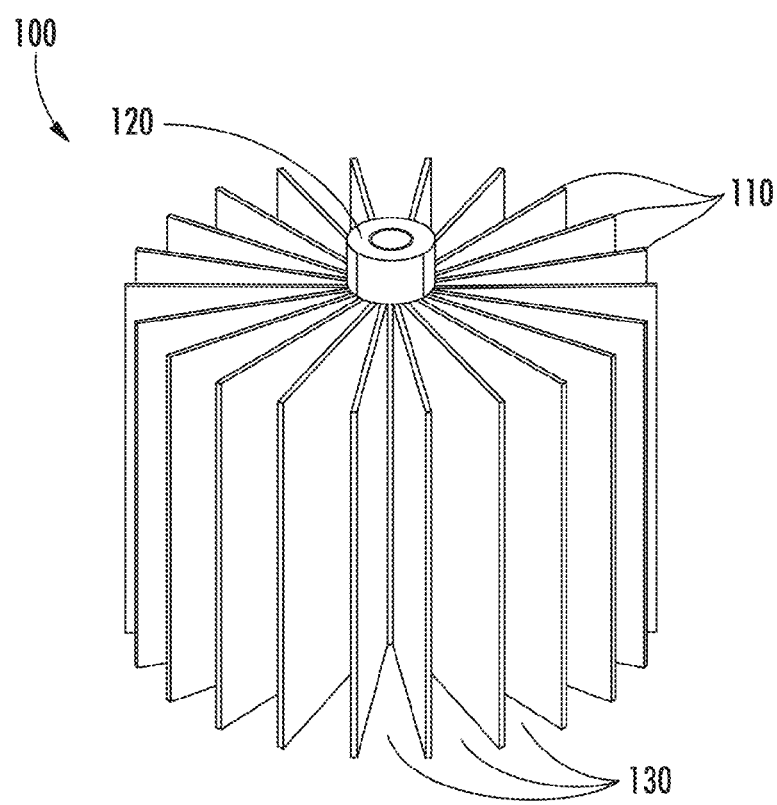
FIG. 1C is a side view of a toroidal bending magnet for hadron therapy.

FIGS. 1A-1C show the geometry of the proposed toroidal bending magnet 100. FIG. 1A shows a view from the top of the magnet 100 (i.e. along the main axis of the torus), while FIG. 1C shows a view from the side of the magnet 100. Multiple plates 110 make the magnet 100 a toroidal bending magnet. The plates 110 may rest against a bucking cylinder 120. There are gaps 130 between the plates 110. One of these gaps 130 is used to bend the beam. Throughout this disclosure, the term "beam" is used to refer to a beam of charged particles. These charged particles may be, for example, protons, ionized elemental molecules, such as carbon, or other ionized species. Further, both positively and negatively charged particles may be used. The rest of the plates 110 contribute to the field in the gap used for bending, and to reduce the stray magnetic field. The additional magnet plates 110 are not otherwise used directly and no beam passes through the gaps 130 between them. Although it seems that a lot of the magnet is wasted, a toroidal magnet system is extremely structurally efficient and is "self-shielded", resulting in devices with much reduced weight. It is best to support the electromagnetic loads on the coils by placing structural plates 110 within the magnet 100, as shown in FIG. 1C. Most toroidal magnet systems (such as those for plasma fusion devices) support these loads elsewhere.

While FIGS. 1A-1C show a bucking cylinder 120, other embodiments are also possible. For example, a wedge configuration may be used where the inner edges of the plates 110 are shaped to support the inward radial forces. In this way, the plates form a self-supporting vault.

The beam may be provided by one particle accelerator or several accelerators. For most applications, the accelerators are cyclic, such as cyclotrons, synchrocyclotrons or similar cyclic accelerators. The cyclic accelerators can be isochronous cyclotrons, synchrocyclotrons, FFGA accelerators and others. In addition to conventional accelerators, the particle accelerator upstream from the unit could be a laser plasma accelerator, which provides particles with a range of energies and a relatively large emittance. The term "particle accelerator" is used to denote any device capable of creating the beam described herein. The accelerated particles can be protons, carbon ions, or other charged species.

In FIG. 1A, the plates 110 are arranged symmetrically around the torus. In other words, the plates are arranged such that the angle between adjacent plates is given by 360° divided by the number of plates. In FIG. 1B, the plates 110a and 110b are arranged in bundles 115, and the bundles 115 are arranged symmetrically around the torus. In other words, the angle between the centers of adjacent bundles is given by 360° divided by the number of bundles. In some embodiments, the bundles 115 may comprise two plates 110. There can be more than two plates 110 in each bundle 115, but the bundles 115 should be symmetrically arranged around the torus (to decrease the stray fields). While FIG. 1A-1B shows the plates 110 extending radially outward from the major axis or center of the bucking cylinder 120, other embodiments are also possible. For example, the plates 110 may not all be radial, as shown in FIG. 10B.

The plates 110 may consist of one pancake winding, or it may contain two (double pancake), or multiple sets of winding, convenient for manufacturing of the plates. A pancake consists of a planar spiral winding of the conductor. In a double pancake, the current leads for the magnet occur at the same location, usually at the outer region of the spiral, with a kink in the conductor in the innermost region of the spiral where the current transfers from one inwardly-directed spiral in one side of the plate 110 to an outwardly-directed spiral on the opposite side of the plate 110. The purpose of the central plate is to provide structural support, as well as cooling, as will be described later.

Figure 20A:
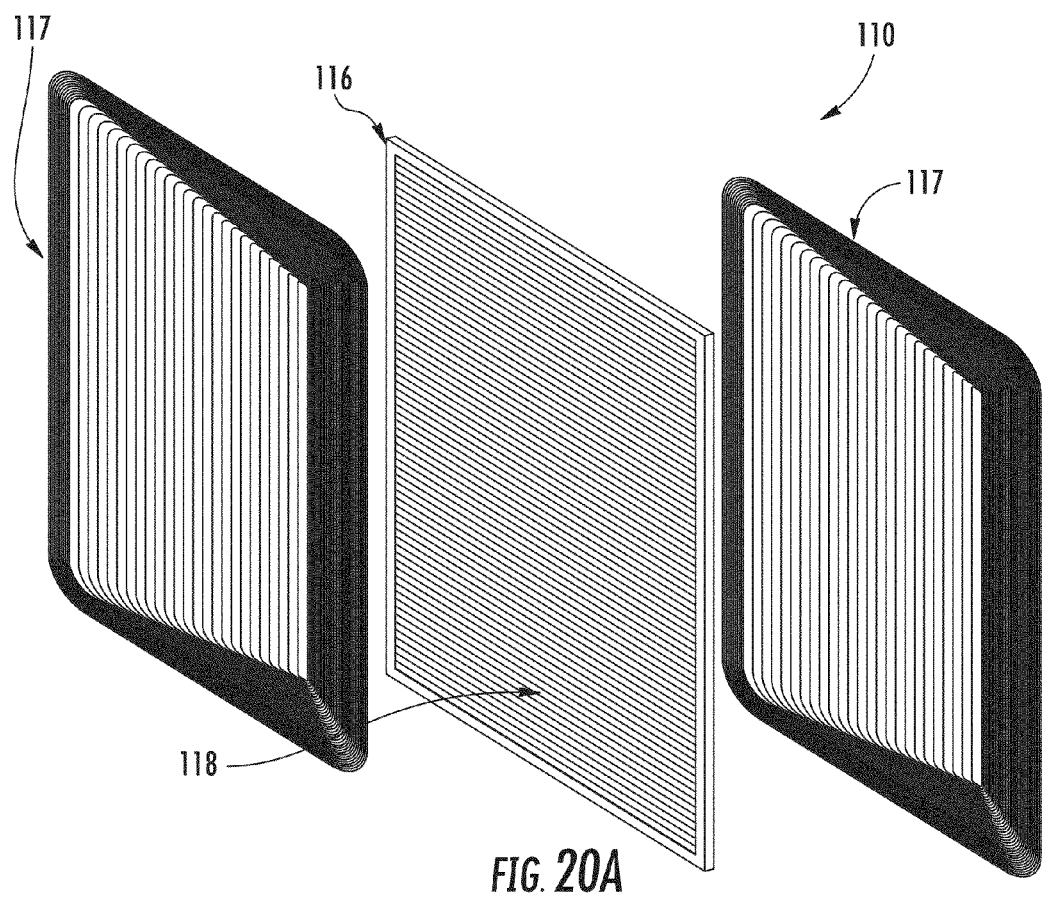
FIGS. 20A-20B show means for construction of a plate, including one flat structural and thermal element, and two pancakes disposed on either side of the flat element.
Figure 20B:
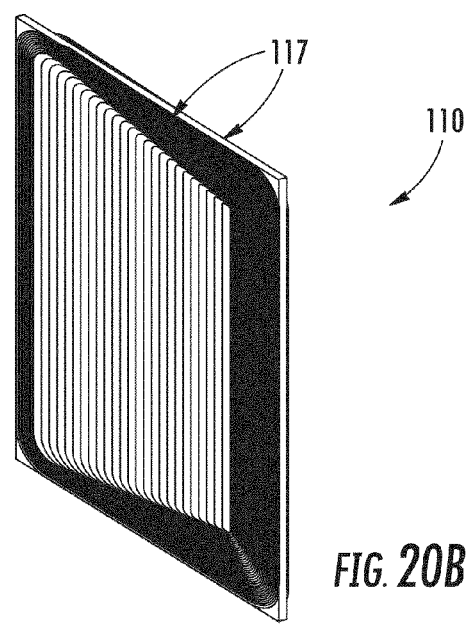

FIGS. 20A-20B show an embodiment of a plate 110 when using two pancakes (double pancake). A flat element 116 is used to separate the pancakes 117 and provide structural support, while also providing conduction cooling. The flat element 116 comprises a non-conducting or highly resistive element, such as glass-epoxy, into which a highly thermally conducting element 118, such as strips of copper or aluminum, is placed. For steady state applications, it may not be necessary to fragment the thermally conducting element 118, but for pulsed application, it is desirable to fragment it, either into strips or strands to minimize eddy current heating of the thermally conducting element 118. The flat element 116 has one conductor pancake 117 on each side. The two pancakes 117 can be arranged so that they have internal connections, as usually done in double pancake windings. The combination of the flat element 116 and either one or more pancakes 117 is referred to as a plate 110. Thus, the plate 110, which is fundamentally flat, contains structural, cooling and conductor components. FIG. 20A shows an exploded view of the plate 110, while FIG. 20B shows the plate 110 after assembly.

In one embodiment, the beam is introduced into one of the gaps 130 between the plates 110 in such a way that the beam, if unbent by the magnetic field, would intersect the main axis of the torus. Thus, the beam may be introduced into one of the gaps 130 at a non-zero angle relative to the main axis of the torus. Further, this non-zero angle may be less than 90°.

Thus, in the absence of beam divergence or chromatic aberrations of the beam, the main axis of the torus is in the same plane as the path of the proton beam. In certain embodiments, the beam has no azimuthal component of velocity (with respect to the main axis of the torus). In other implementations, the beam could be introduced parallel to the major axis, at one end of the torus close to the major axis of the torus and exit from the gap 130 between adjacent magnet plates 110 in the periphery of the torus. In still other implementations, the beam could be introduced in the bore of the magnet and extracted either at the outside region or reflected back to the bore of the magnet.

Although the plates 110 shown in FIGS. 1A and 1C are shown as rectangular (i.e., near racetrack shape), the plates 110 can have arbitrary shapes, depending on the particular design objectives. The shape of the plates 110 that make the coils in the magnet 100 can be adjusted so that the regions not needed for beam bending can be eliminated, decreasing the weight and stored energy of the magnet system. Alternatively, the regions of the magnet 100 not needed for beam bending can be adjusted to be far from the beam trajectory so as to not affect beam quality. The thickness of the plates 110 can also be adjusted to maximize their structural efficiency, while minimizing system weight. The plates 110, however, need to be placed in toroidal configuration.

Conventional toroidal magnets have a 1/r field dependence, where r is the major radius of the torus (measured from the main axis of the torus). The 1/r dependence results in non-uniform field that affects the beam optics. This non-uniformity is undesirable for beam bending, especially when the beam is introduced axially into the torus and bent so that it leaves the torus at an angle with respect to its principal axis. This 1/r field variation has dissuaded the use of toroidal magnets as bending magnets for Hadron beam therapy.

In one embodiment, the magnetic field is held constant or nearly constant by the use of magnet plates where the current distribution in the plates is adjusted to minimize the radial variation of the magnet field.

In other embodiments, the current density in the magnet plates in the is distributed to obtained desired properties of the beam, such as focusing, while still performing a bending function.

Figure 2:
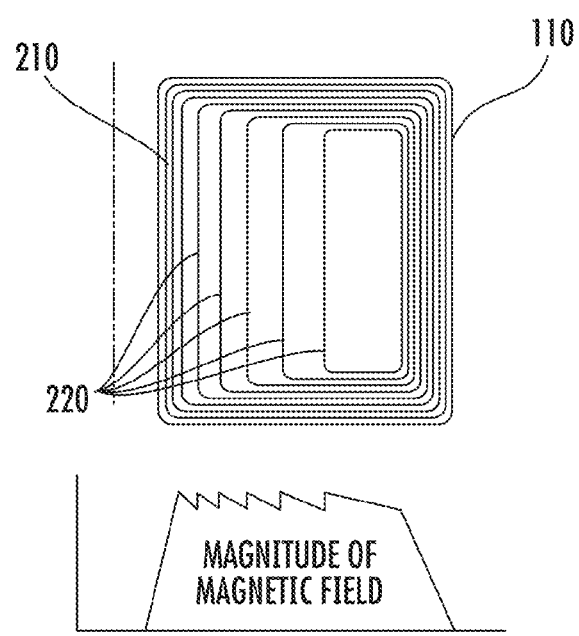
FIG. 2 is an illustration of a plate for a toroidal magnet generating constant magnetic field.

Radial plates with distributed current density can be used to provide a constant magnet field as shown in FIG. 2. The conventional turns 210 generate a toroidal field which, if not modified, would decay as 1/r. However, the introduction of additional turns 220 spaced at defined intervals across the plates 110 allows for the generation of a nearly constant field. The constant field can be used for bending the beams in a manner that is more controlled than if the field decreases with 1/r, especially if the beams are introduced parallel to the major axis of the bending magnet. The separation of the turns 220 can be adjusted to achieve the desired magnet profile along the proton path. Throughout this disclosure, the term "constant field" is meant to denote a magnetic field that is constant or nearly constant throughout the region, where "nearly constant" denotes that the magnetic field varies by less than 25% in the region. However, in certain embodiments, it may be beneficial to have the constant field may be more uniform than this threshold. For example, in certain embodiments, the magnetic field within the constant field may vary by less than 10%. In other embodiments, the magnetic field within the constant field may vary by less than 5%.

Figure 19:
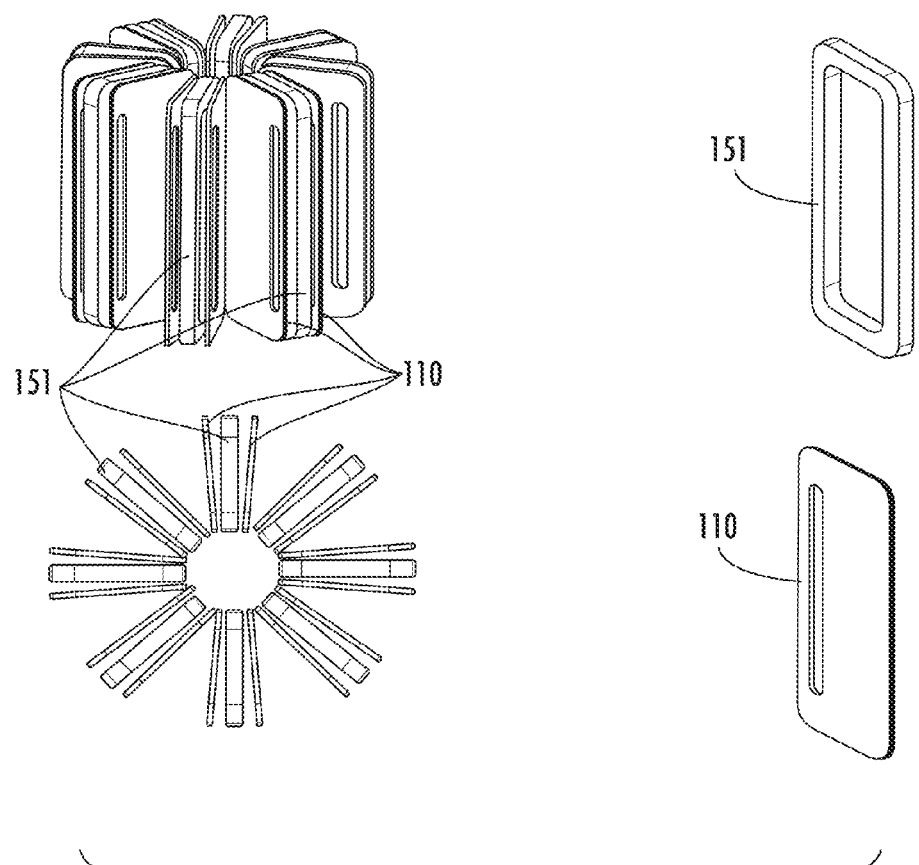
FIG. 19 shows a means of constructing a constant toroidal field magnet, where discrete coils are used to generate the 1/r field, and plates are used to modify the field to approximately constant field.

In another embodiment, shown in FIG. 19, the desired constant toroidal magnetic field profile may be generated by installing distributed-current-density magnet plates 110 (like those shown in FIG. 2) inside of a conventional toroidal magnet array. The toroidal array would be comprised of conductors wrapped on shell-type coil forms. The coil forms 151 would be rigidly linked together to support electromagnetic loads on the toroid, while the constant-field plates 110 would be used as before to minimize the radial variation of the magnet field. The near continuous toroidal shell structure in the inner region of the magnet would minimize construction costs while providing the sufficient structure to mechanically support the magnet plates in a stable configuration.

Achromatic Bending Configuration

Figure 3:
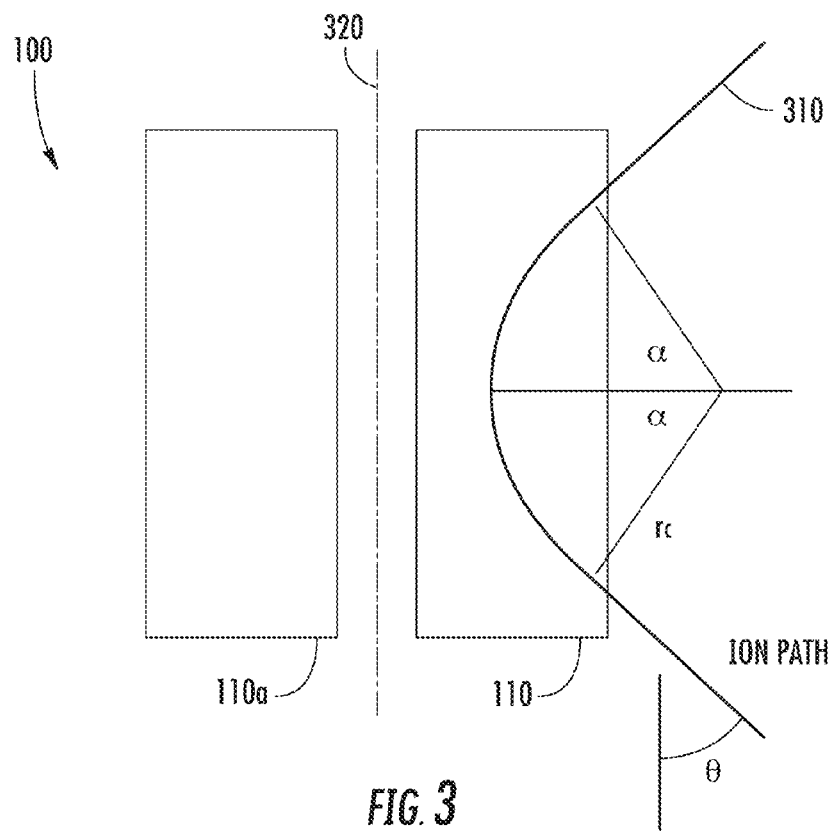
FIG. 3 shows the path of charged particles being deflected by the toroidal bending magnet.

A preferred embodiment of the toroidal bending magnet occurs when the beam is introduced as shown in FIG. 3, where the beam trajectory lies in an r-z plane that also contains the major axis of the torus. Instead of introducing the beam at one end of the toroidal bending magnet, the beam 310 is introduced into the gap from the outer region of the toroidal bending magnet, at an angle θ to the major axis 320 of the torus, where θ is greater than 0° and less than 90°, with respect to the major axis of the torus. Only two plates 110, 110a of the torus are shown in FIG. 3 for simplicity. The beam 310 comes from the outside of the torus and is bent back to the outside of the torus.

This approach has several advantages. The angle of exit of the beam 310 with respect to the major axis 320 of the magnet is exactly opposite from that at the entrance, by symmetry. Thus, if the beam 310 has charged particles of multiple energies, the angle of exit of the charged particles with different energies come out at the same angle, although at different axial locations. Similarly, if different energy beams are used in sequence, for example for varying the penetration depth of the beam in a treatment procedure, the charged particles come out at the same angle (but the axial exit location shifts with the energy).

Figure 4:
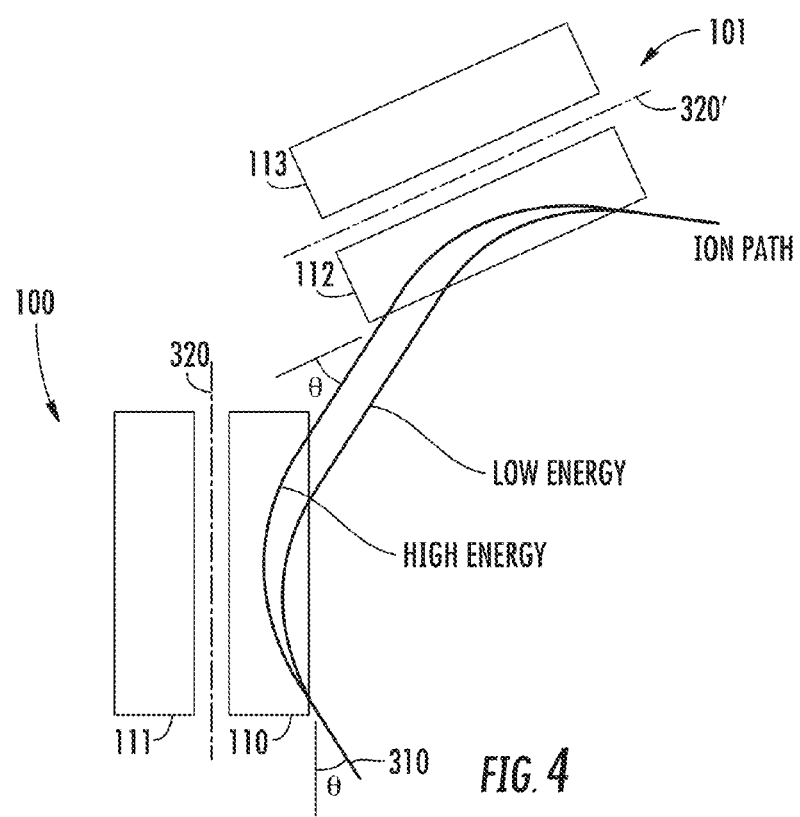
FIG. 4 is an achromatic toroidal magnet set composed of two toroidal bending magnets.

A second toroidal bending magnet 101 can be placed downstream from the first magnet 100, such that the angle of exit of the beam 310 from the first magnet 100 is the same as the angle of entrance into the second bending magnet 101, as shown in FIG. 4. FIG. 4 shows two plates 110 and 111 from the first magnet 100 and two plates 112 and 113 from the second magnet 101. The first magnet 100 has a major axis 320, while the second magnet 101 has a major axis 320'. By symmetry, and without the need of computations, it is easy to determine that, in the bending plane, charged particles of different energy, which were spread out by the first bending magnet 100, are collected back together by the second bending magnet 101. Thus, the set of bending magnets are achromatic (i.e. the magnets bend the beam in such a manner that charged particles of different energy that enter the magnet set at the same location and the same angle exit the second magnet at the same location and at the same angle).

One further advantage of the injection topology used with achromatic toroidal bending magnet set is that the field in the magnet does not have to be constant. As long as the magnetic field profile is constant in the axial direction of the torus, so that the field profile of beam as it penetrates into the torus are the same as when they exit, the achromaticity of the magnet set is maintained.

Detailed Description of the Toroidal Bending Magnets

To minimize the weight of the toroidal bending magnet, the aspect ratio of the torus should be as small as technically feasible. Thus, the inner legs of the magnet plates should be close to the main axis of the torus. The reason for this is that only the radial extent of the plates is used for beam bending. Because the system weight is a strong function of the outer radius of the magnet, both the outer radius and the inner radius of the torus should be as small as possible. For this configuration, the otherwise strong magnetic field dependence with radius makes the use of distributed current across the width of the plates (as shown in FIG. 2) very attractive to generate the uniform magnetic field required in the gaps between plates 110.

It can easily be shown that the angle of bending $2\alpha$ is equal to twice the angle $\theta$ formed between the beam and the major axis of the torus, or $2\theta$ in FIG. 3. As long as the angle of the incoming beam 310 with respect to the axis of the second toroidal bending magnet 101 is the same as for the first bending magnet 100, the achromaticity of the beam bending is satisfied within the bending plane. It should be noted that if the second toroidal magnet 101 is placed at an angle of $-\theta$, the separation of different charged particles with different energy will be doubled, not cancelled. Thus, achromatic toroidal bending magnet should be coupled in pairs, with each pair set at the same angle. More than one pair is possible in a beam line.

The magnetic field determines the radius of curvature of the beam. Assuming that the radius of curvature of the beam is $r_c$, as shown in FIG. 3, then the length of the active region of the toroidal bending magnet is $\sim 2\, r_c \sin \theta$. The lower the magnetic field, and thus the longer $r_c$, the longer that the active region of the toroidal bending magnet needs to be. Similarly, the radial extent of the toroidal bending magnet is:

$$r_c(1-\cos \theta)$$

The larger $r_c$ (either due to high beam energy or lower magnetic field), the deeper in the torus that the beam 310 will penetrate. Increasing the magnetic field in the bending magnet would decrease $r_c$ and the depth and required axial length of the magnet.

It should be noted that the fringing fields in the toroidal magnet (that generate ripple in the magnetic field) result in a focusing-defocusing magnet set (in the azimuthal direction). The field profiles, and the focusing defocusing, can be adjusted by selecting appropriate separation between the turns in the plate. The focusing/defocusing occurs only in the bending plane, so a secondary set of magnets may have to be introduced to minimize dispersion of the beam in the transverse direction to the bending plane (in the azimuthal direction). Focusing quadrupoles may be desired upstream and/or downstream from the bending magnet. It is possible that only azimuthal corrections are required, reducing the number of quadrupole focusing magnets required (conventional magnets required sets of two quadrupole focusing magnets, for beam dispersion correction in planes normal to each other).

Calculations of the magnetic field profile that can be generated with torus are now presented.

Figure 5A:
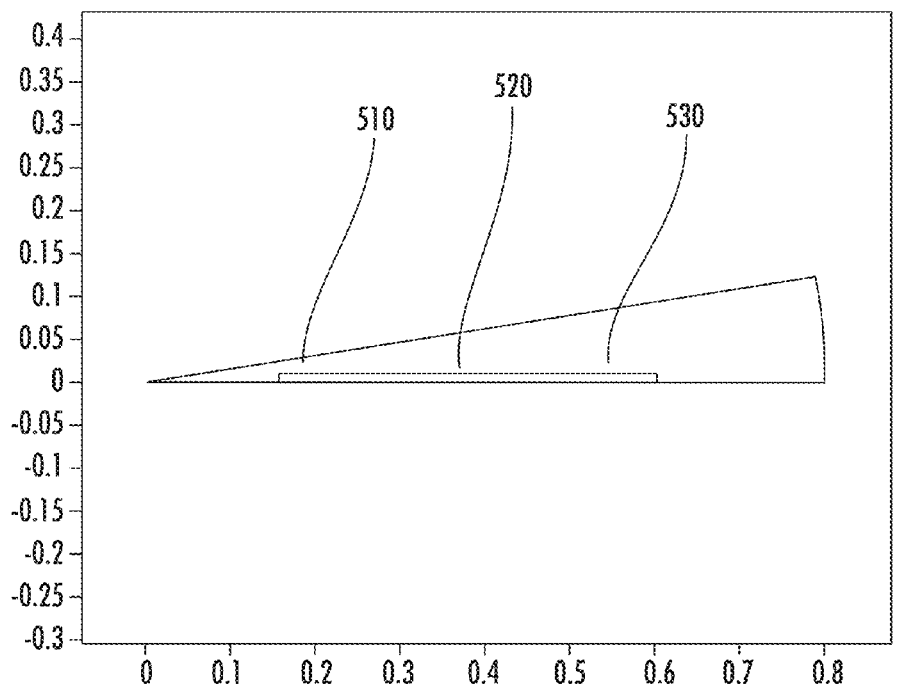
FIG. 5A shows a pie-section of a toroidal field magnet (midplane), showing one pancake coil.
Figure 5B:
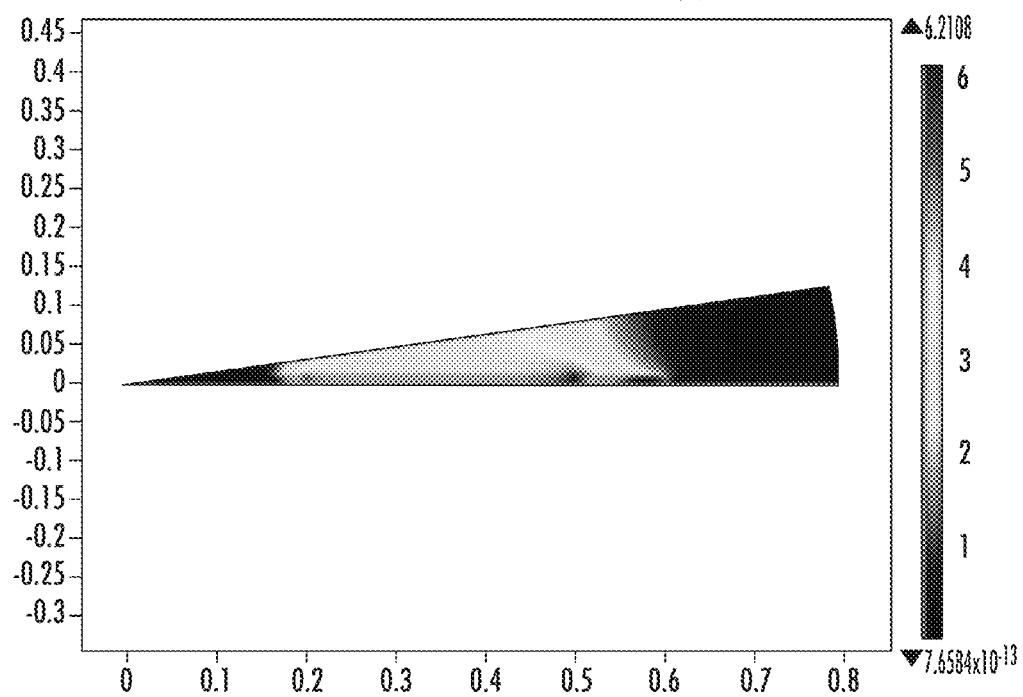
FIG. 5B shows the resulting magnetic fields.

One possible method to construct the toroidal field is to place the conductor in a double pancake configuration, each pancake 117 attached on a respective side of the flat element 116, which serves as a structural/cooling plate. FIGS. 5A-5B show the geometry and the resulting magnetic field contours at the midplane of the magnet, respectively. In FIG. 5A, only one pancake is shown, and symmetry plane boundary conditions are used at both sides of the pie-shaped geometry. Each pancake contains three sections: the innermost section with high current density in the throat of the magnet, which builds the toroidal field quickly, also referred to as the field-building region 510. The second section, is disposed outward from the field-building region 510, and has lower current density (turns in the pancake separated from each other to decrease the current density), and is used to eliminate the 1/r variation in the magnetic field intensity in this region. This second section is referred to as the constant field region 520. As described above, the constant field region 520 has a magnetic field that is constant or nearly constant throughout the region. In certain embodiments, the magnetic field varies by less than 25% within the constant field region 520. In other embodiments, the magnetic field varies by less than 10% within the constant field region 520. In yet other embodiments, the magnetic field varies by less than 5% within the constant field region 520. The return leg of the turns is again high current density, but with current flowing in the opposite direction, to minimize fringe magnetic field outside the torus and return the current from the other two regions. This section, which is the outermost region is referred to as the return current region 530. The resulting magnetic field is shown in FIG. 5B, indicating that the magnetic field is nearly constant across most of the gap. In addition, it should be noted that the magnetic field outside of the torus is very small, and decreases very rapidly with radius (not shown, as the fields are very small).

Figure 6A:
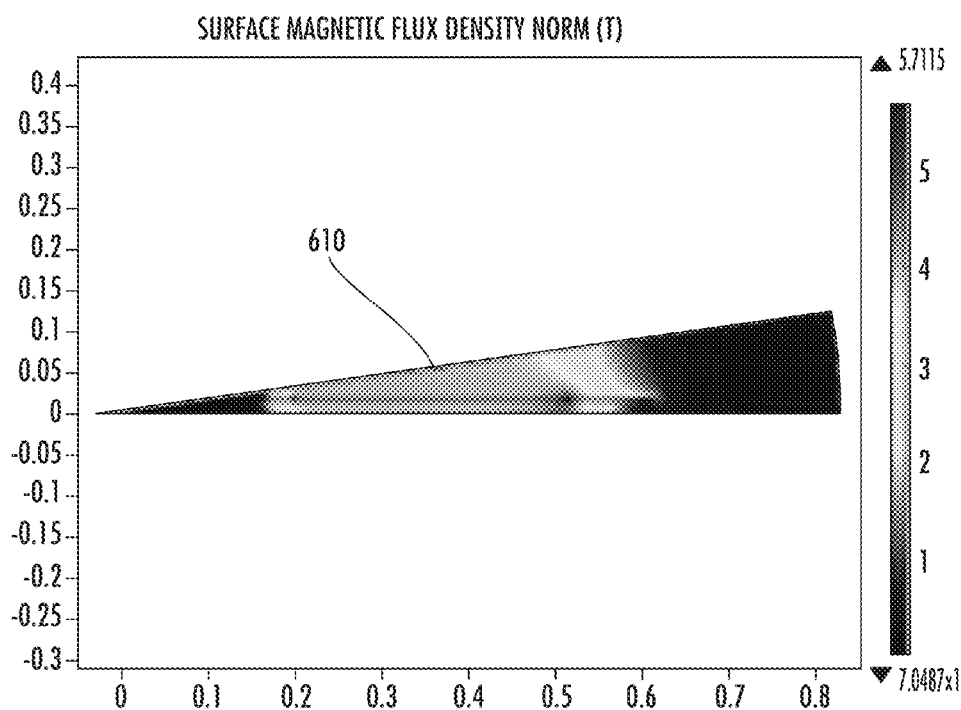
FIG. 6A shows the magnetic field profile when the distance between the pancakes is increased.
Figure 6B:
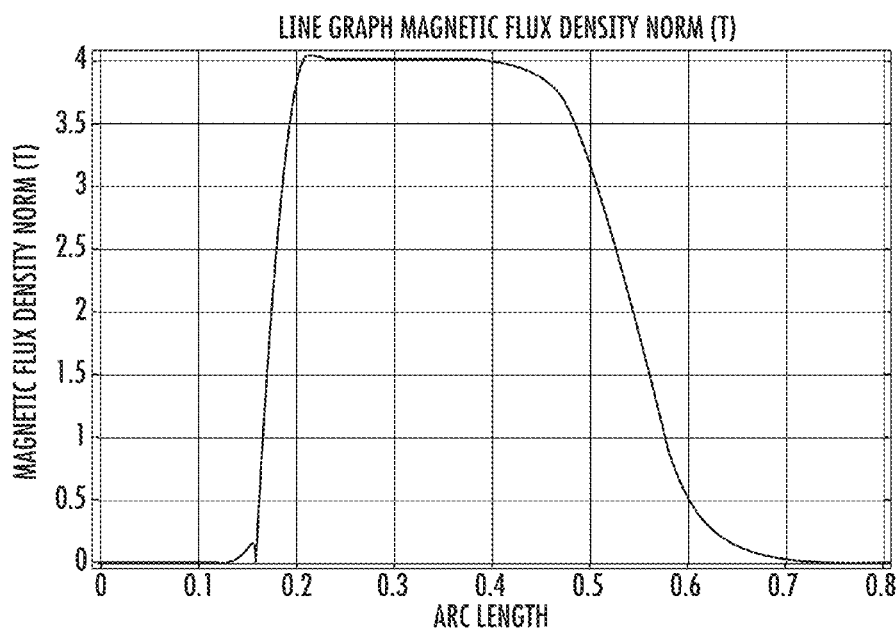
FIG. 6B shows the resulting magnetic field profile along the mid-plane radius centered between two adjacent coils.

FIGS. 6A-B show the result when the gap between pancakes is increased, with the resulting field profile as a function of radius in the region between coils. FIG. 6B shows the resulting magnetic field profile along the midplane radius centered between two adjacent coils (corresponding to the line 610). The magnetic field is nearly uniform in the constant-field region, with field decreasing quickly with radius at the outer region. In FIG. 6A, it is intended to use the space adjacent to line 610 as the region used for the beam channel. In the case where the beam is injected along 610, the beam channel can be made substantially wider near the outer region of the magnet.

Figure 7:
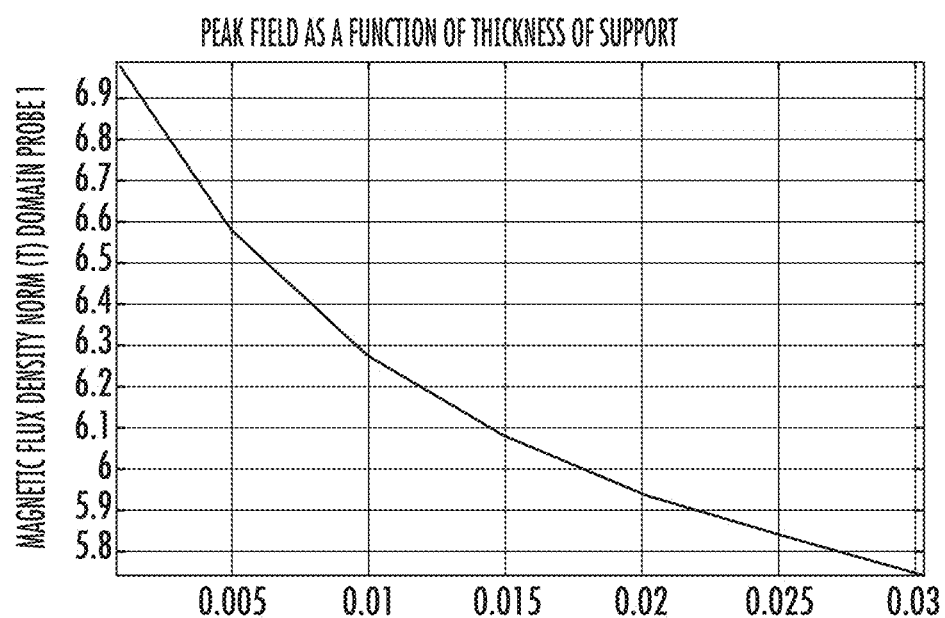
FIG. 7 shows the dependence of the peak magnetic field as a function of the gap between the double-pancakes in the toroidal field coil.

However, it is clear from FIGS. 5A-B and 6A-B that the peak magnetic field at the conductor in the return current region of the coil is substantially higher than the field in the uniform region. The peak magnetic field can be reduced by modifying the location of the pancakes and the current density in the pancake in the plates. FIG. 7 shows the dependence of the peak field as a function of the gap between the pancakes in the double-pancake arrangement that makes the magnet. When the gap between the two pancakes in a double-pancake is relatively large, instead of using a single plate to contain both of them, it may be more efficient to separate the pancakes and to use one structural plate per single pancake, reducing weight.

Figure 8A:
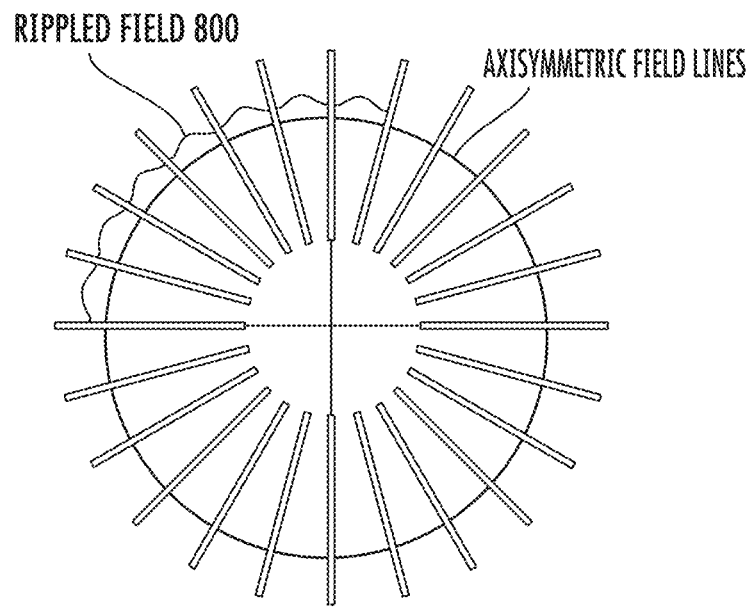
FIGS. 8A-B show the possibility of changing the ripple characteristics in the outer region of the toroidal field coil by adjusting the gap and angle between plates.
Figure 8B:
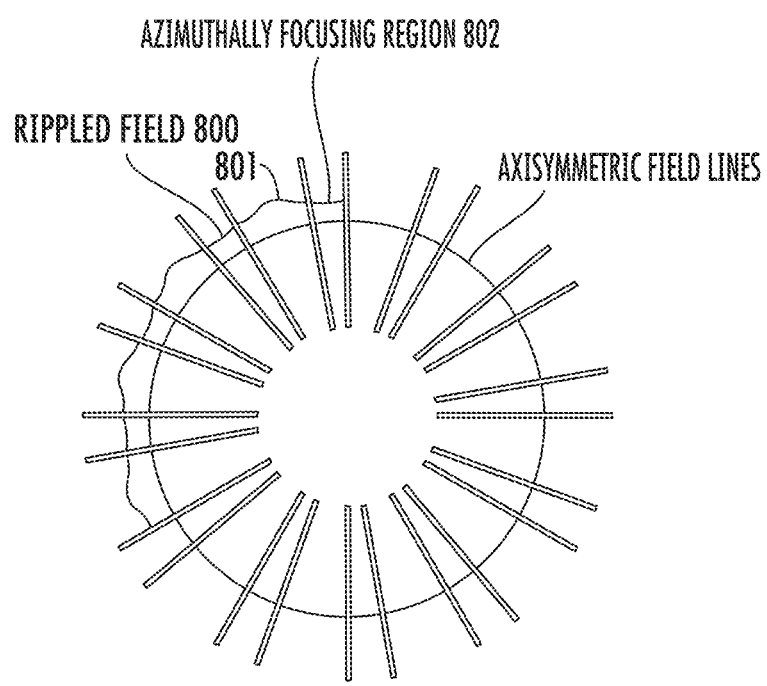

Although only the gap between the pancakes has been varied in FIG. 7, it is possible to also adjust the angle between the pancakes. By doing this, it is possible to have either bulging magnetic fields or reverse-bulging fields, as indicated schematically in FIGS. 8A-8B. The configuration in FIG. 8A shows uniformly placed pancakes, where the rippled field 800 bulges outward from the major axis. The configuration in FIG. 8B shows the pancakes placed in pairs, where the angle between the pancakes in a pair is less than the angle between adjacent pairs. In this configuration, the rippled field 801 between adjacent pairs is bulged outward, where the rippled field 802 between two pancakes in the pair is rippled inward. The azimuthal variation in rippled field 800 also has marked effect on transverse dispersion of the beam.

Figure 9:
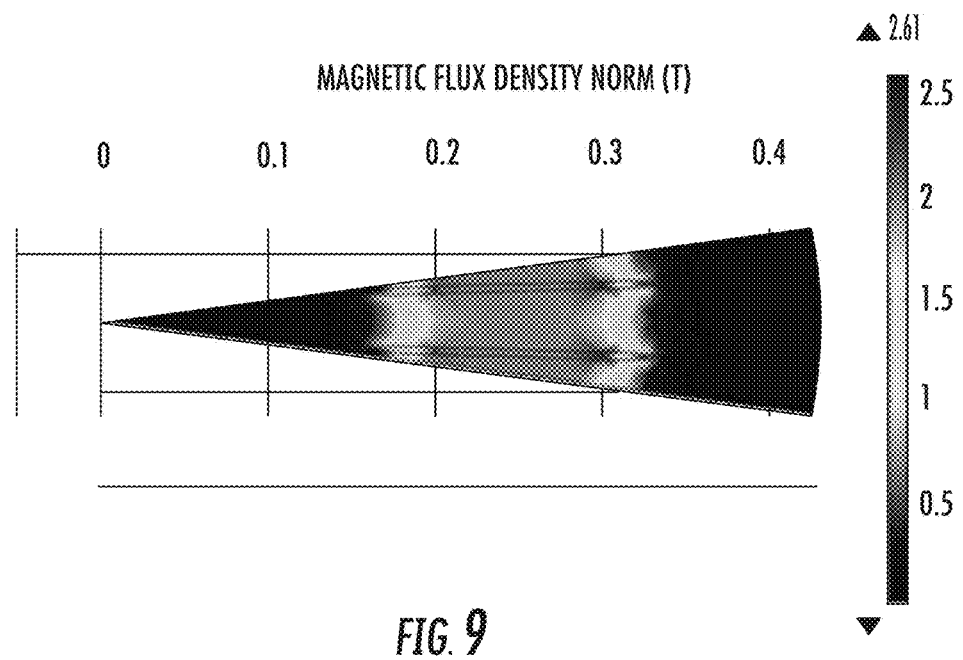
FIG. 9 shows the magnetic field contours for the case of higher current density in the return leg.

Decreasing the peak field on the conductor goes hand-in-hand with decreasing the ripple of the field. The field ripple, as will be shown below, has impact on the beam optics, as the field gradients have focusing/defocusing characteristics. In addition, it is also possible to modify the characteristics of the field in the outer region by modifying the return current of the coil. FIG. 9 shows the results of the calculations for the case of increased current density in the return region of the coil. The horizontal axis represents the radius of or distance from the major axis of the torus. In FIG. 9, the field profile for both pancakes is shown. The model is assumed periodic, with 20 periods in the toroidal direction. The number of periods can also be adjusted. In addition, the magnetic field in the active region has been reduced, from 4 T in previous Figures to 2 T in FIG. 9. In FIG. 9, the innermost layer (that builds up the magnetic field (corresponding to 210 in FIG. 2) carries 50 kA per pancake, the region that maintains constant magnetic field amplitude (corresponding to 220 in FIG. 2) carries 25 kA per pancake and the return leg (carrying the return current in the outermost region of the magnet carries 75 kA per pancake.

With 20 periods, the stray field away from the toroidal field coil decreases as $1/r^{19}$. Thus, very low stray field can be enabled by the use of the toroidal bending magnet. The limited use of some iron may assist in decreasing the relatively small magnetic field very close to the magnet, if needed. However, in other embodiments, no iron or other ferromagnetic material is used to construct the magnet.

Illustrations of the beam characteristics when interacting with a toroidal bending magnet are presented next. It is assumed that the magnitude of the field of the constant field section of the field is approximately 2 T, and that the charged particle velocity is about $1.71 \, 10^8$ m/s (corresponding to a beam energy of roughly 200 MeV). The angle of incidence is 30 degrees, so the total bending is 60 degrees. The beams are injected in a radial plane. The initial beam cross section is 0.5 cm radius, and the beam has no divergence.

Figure 10A:
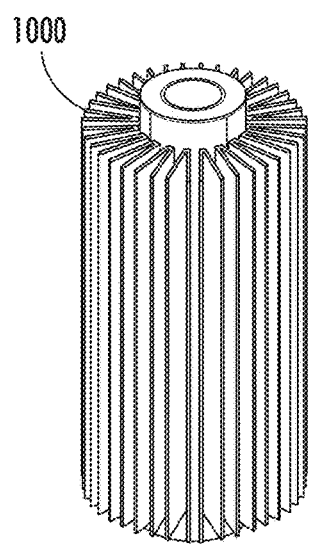
FIGS. 10A-10B illustrate the toroidal field magnet of a toroidal bending magnet.
Figure 10B:
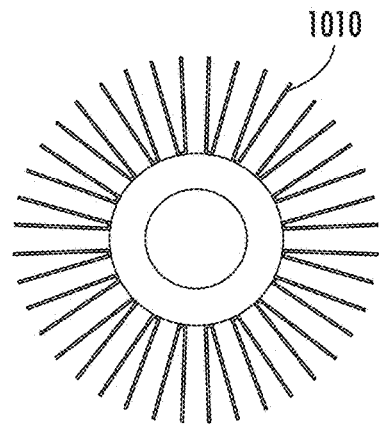

A schematic of the magnet 1000 is shown in FIGS. 10A-10B. The cross section of the magnet 1000 actually corresponds to that in FIG. 9, with plates 1010 that are not radial. The beam is injected in between two plates 1010 in the region with minimized field ripple. The radial extent is small, as the charged particles do not penetrate deep radially into the coils, and thus, by minimizing the radial extent, the size/weight of the magnet is decreased. Instead, the height of the magnet is substantial, as the charged particles propagate about 1 m in the axial direction. The example has been calculated using a 2 T field (as shown in FIG. 9). Higher fields would further reduce both the radial and the axial dimensions of the magnet.

Figure 11A:
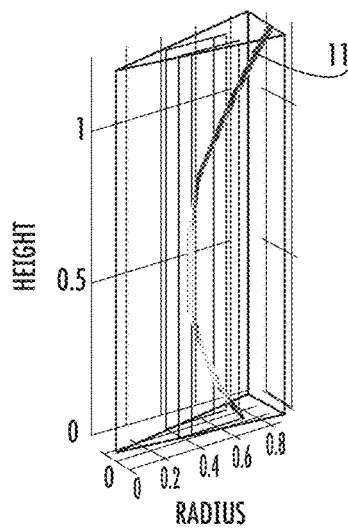
FIGS. 11A-11B show the beam path as it moves across the toroidal bending magnet.
Figure 11B:
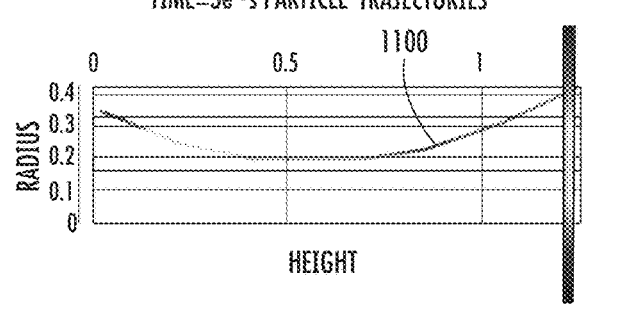

FIGS. 11A-11B show the results of the calculations for a beam with a velocity of $1.71 \times 10^8$ m/s across the magnet. The beam 1100 is bent 60 degrees. The active length of the magnet can be shorter than about 1 m. The initial radius of the beam 1100 is 0.5 cm, with no divergence. The outermost radius of the coil is 0.33 m, and the section with constant field amplitude is between radii of 0.2 m and 0.3 m. As described above, the exit angle is the same as the inlet angle. Note that the beam 1100 is compressed (i.e., focused) in the radial direction in the region of the beam path that is at the smallest radius.

However, the beam dimension (in the place of the beam propagation shown in FIG. 11B) returns to close to the original beam width at the exit of the toroidal bending magnet. FIG. 11B is in the z plane, where z is the axial direction of the toroidal bending magnet and x is in the radial direction in the midplane between the two plates that surround the region of the beam entrance. The average beam path is also in the zx plane.

Figure 12:
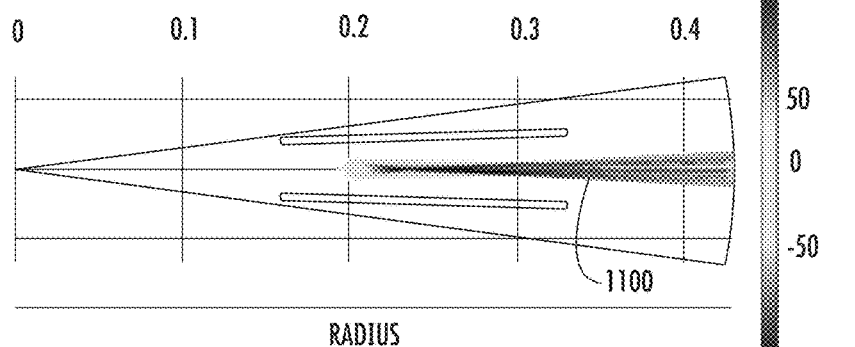
FIG. 12 shows the beam profile for the case shown in FIGS. 11A-11B, but in elevation view.

The problem associated with the ripple is illustrated in FIG. 12. The same results as shown in FIG. 11 are shown in FIG. 12, but as an elevation view. The beam 1100 spreads out in the azimuthal direction. The spread is associated with the ripple of the magnetic field, and the spread has been decreased by adjusting the location and orientation of the plates in order to minimize the ripple (which also decreases the azimuthal spreading of the beam). Clearly, there is a transverse defocusing of the beam as it leaves the torus. The spreading can be adjusted by modification of the magnetic field in the gap, that is, by adjusting the current density in the plates (by adjusting the separation between the turns 220), the location of the plates (orientation and gap), and by modification of the plates themselves and in particular the return current path. The outer region of the magnet is defocusing, but the inner region (at small radii) is focusing. Indeed, the net effect is a relatively strong focusing of the beam, with a focusing at a radius of about 0.24 m, and then beam defocusing beyond this point.

In addition to field modification, it is possible to adjust the characteristics of the beam. For example, the beam can be focused prior to entering the toroidal bending magnet by one or more quadrupole focusing magnets so that the emerging beam is parallel at the exit, instead of diverging. Although the focusing magnet can be placed in the region when the beam emerges from the bending magnet, it is not convenient for variable energy, as will be shown below. Alternatively, the focusing at the small radius can be made to match the defocusing from the entering beam, with no net focusing. However, this solution works for a narrow energy spread. Beyond that, it would be necessary to adjust the strength of the magnetic fields of the bending magnet.

Figure 13:
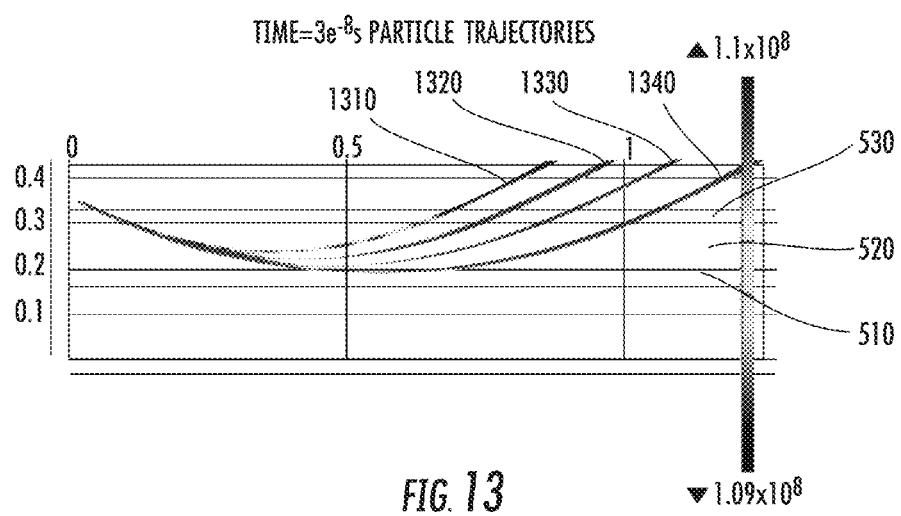
FIG. 13 shows the path (in the average plane of the beam) for several beam velocities and energies.

The effect of changing the proton velocity on the beam propagation is shown in FIG. 13. Several particle velocities have been assumed: 1.1, 1.3, 1.5 and $1.7 \, 10^8$ m/s, corresponding to lines 1310, 1320, 1330 and 1340 in FIG. 13, respectively. The energy spread is about a factor of 2.5. The paths of the beams are shown passing through different regions of the magnet: field-building region 510, the constant field region 520 and the return current region 530. Outside of return current region 530, the beam is outside of the magnet, and as shown in FIG. 13, the beams of different energies, although displaced axially, are coming at the same angle, as described above. The higher energy beams penetrate further radially into the magnet, as expected. The highest energy determines the required radial width of the toroidal bending magnet, at least the section with relatively uniform fields. Because the exit axial location of the beam varies with energy, it is more expedient to perform the required manipulation of the beam upstream of the magnet, where the location and direction (orientation) of the beam is the same, irrespective of the beam energy. It should be noted that focusing of the beam in the radial direction occurs naturally for all beam energies.

Figure 14:
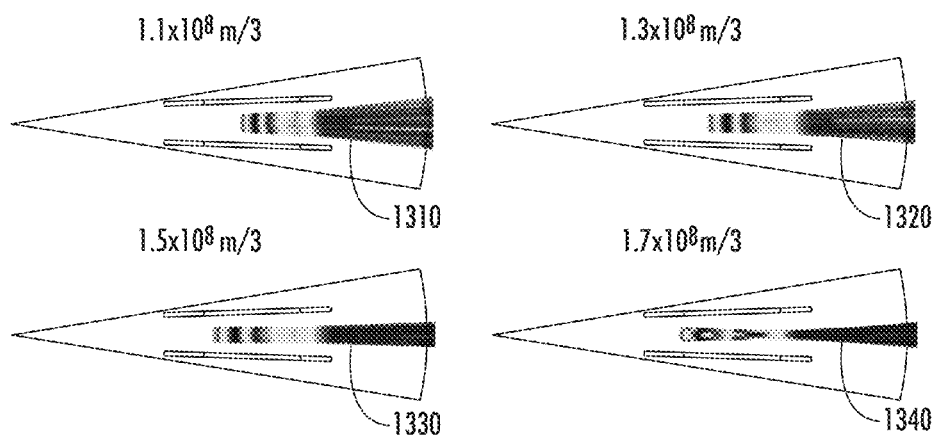
FIG. 14 shows elevation views of the beam and the magnets for different beam velocities.

FIG. 14 shows a top view of the beam of different velocities (and thus energies). The azimuthal beam size increases with decreasing energy. Somewhere between $1.5 \times 10^8$ and $1.7 \times 10^8$ m/s, the beam emerged from the toroidal magnet without divergence. The toroidal bending magnet compensates for the defocusing in the outer region of the magnet (near the entrance and exit locations) by focusing in the inner region, near where the beam travels parallel to the main axis. The proton beam at the exit goes from defocusing to focusing, at this energy.

If the beam is smaller than the assumed 1 cm diameter, the divergence of the beam would be smaller than indicated in FIG. 14.

Estimates of Toroidal Magnet Parameters

Figure 15:
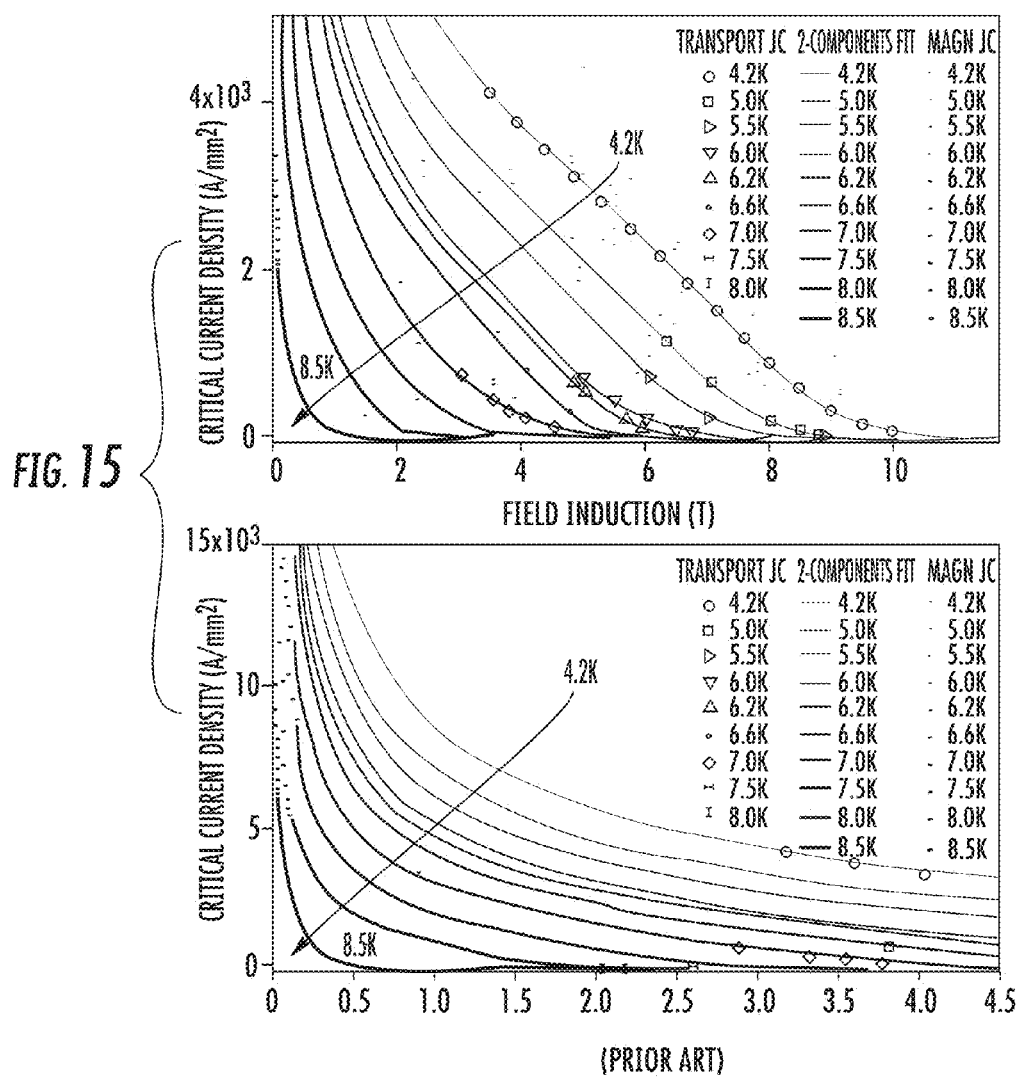
FIG. 15 shows the critical current density in NbTi as a function of field for different operating temperatures.

The main characteristics of the toroidal magnet described in FIGS. 9-10 are described below. Assuming that 0.75 mm diameter NbTi strands are used for the magnet at a peak field of 3 T (for a constant field region of 2 T, as shown in FIG. 9), the current density in the strand at 4.2 K is ~4000 A/mm^2, as shown in FIG. 15. With a 60% operating current margin relative to the critical current, and superconductor area fraction of 50%, the operating current per strand is thus about 530 A. If a Rutherford cable is made from 6 strands of NbTi and 6 strands of copper, the size of the cable is about 2 mm thick by 4.5 mm wide. The Rutherford cable is wound with bending in the easy direction, and place in the grooves of the structure. In the field-building region 510 in the inner region of the magnet, the total current is 50 kA. Thus, about 16 turns are required in this zone. Similarly, in the constant field region 520, each pancake (carrying 25 kA) needs 8 turns. The return current region 530, of course, carries the same number of turns as the two above combined, or 24 turns. For 20 plate toroidal magnet built using 1 m tall magnet plates with radial width of 0.15 m, the total required volume of conductor is about 290 cm$^3$ of SC/copper, for a total mass of conductor (for all 40 pancakes) of 95 kg.

Toroidal bending magnets are attractive in that they are structurally efficient. The minimum required structure can be readily calculated using the Virial stress. The total stored energy in the magnet described in FIGS. 9-10 is about 500,000 J. Assuming a stress of about 200 MPa (high strength aluminum with a large safety margin), the required cross sectional area is about 25 cm$^2$. The required thickness of the structure in each plate needs to be substantially less than 1 mm to support the in-plane stresses. The thin plate would have problems with rigidity and warping out-of-plane, and thus it assumed that the plates are thicker, about 2 mm thick. In this case, the minimum required weight for all 40 plates would be about 90 kg. Additional structure (struts for a torque frame) are required to support the electromagnetic loads between the magnet plates, but even doubling the weight of the structure, the total weight of the magnet is still only about 300 kg. Other design considerations, such as: operation at higher than 4.2K peak temperature, a need to reduce mechanical stress concentrations in the structure, provision for cryogenic cooling of the plates, handling considerations during manufacture, need to provide mechanical stiffness greater than magnetic stiffness, and quench and/or fault handling considerations, may all require slightly more massive structure than indicated by the preliminary calculations presented here.

To properly position the turns, the conductors should be placed in grooved support plates. The grooves could be machined into the plates, cast with the plates, or applied using an additive process like 3D printing. Alternatively, the grooves could be formed into plastic sheets secured to the thin metal support plates. The conductors can be secured by the use of clamps, cover plates, or adhesives. The grooves can be present on one side of the plates, or on both sides as in a double pancake winding. Double pancake windings have the added advantage that all interconnects between plates can be made near the outer diameter of the toroid, where access is easier.

The example presented here assumed a double pancake arrangement with a periodicity of 20. Lower periodicity (and reduced number of plates) would result in improved rigidity of the plates. There is substantially more structure than needed to take the in-plane loads, and thus, higher field operation would not necessarily require increased weight due to larger structure.

The calculations above are illustrative. Alternative magnet arrangements can be used to further optimize the system.

Figure 16:
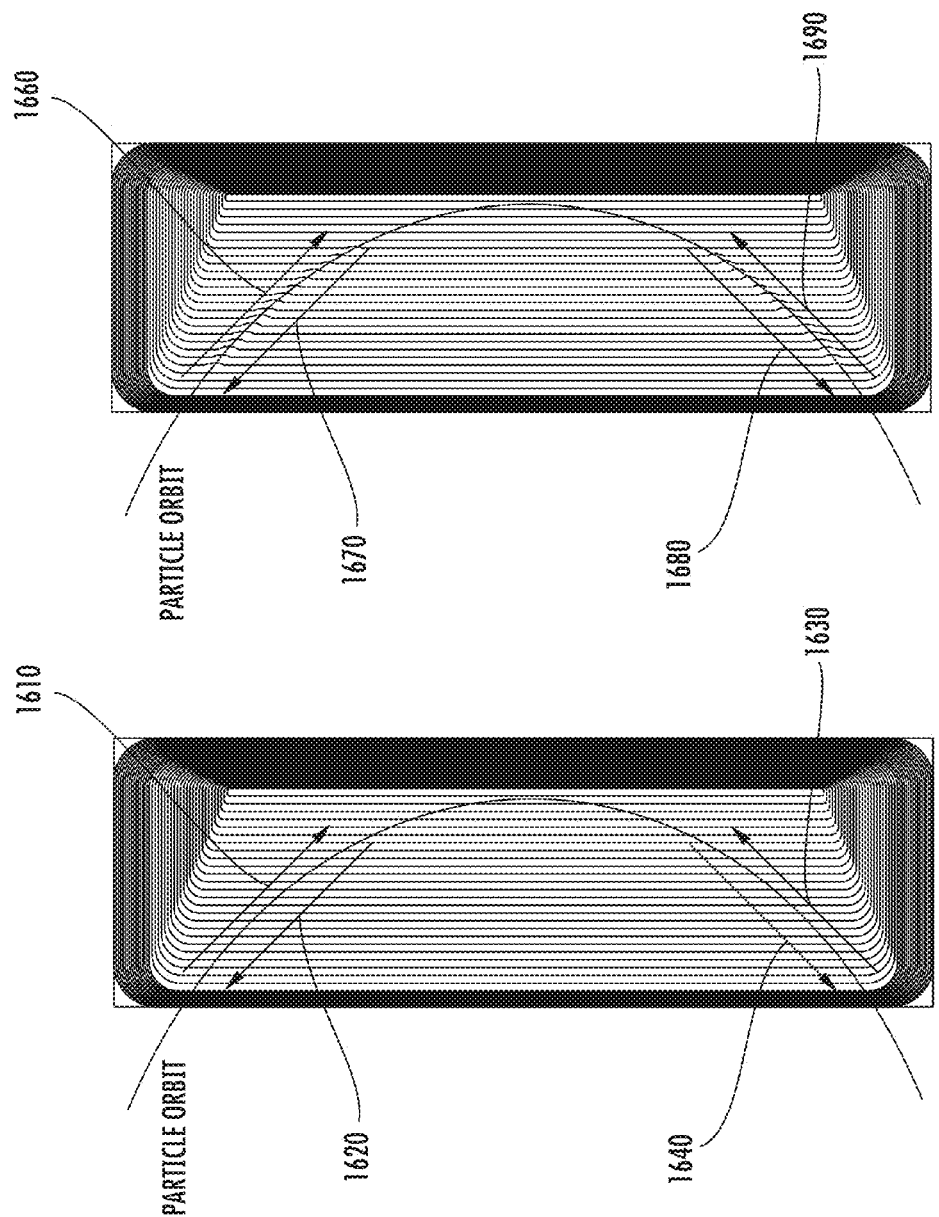
FIGS. 16A-16B show the introduction of quadrupole focusing magnets by local adjustment of the turns in the plates.

One additional embodiment of the toroidal field magnet is illustrated in FIGS. 16A-B. Quadrupole field variations can be introduced into the system by modifying the winding in the constant field region 520 of the magnet. FIG. 16A shows the desired current that would be needed to superpose a quadrupole field on top of the constant, beam bending field. Opposite currents 1610 and 1620 on the upstream section of the plate, and opposite currents 1630 and 1640 in the downstream section of the plate, would produce a quadrupole field that could be used to focus the beam. The desired current direction in one of the plates is shown. The adjacent plate (on the other side of the beam) would have the opposite currents, for a quadrupole configuration. One way to achieve the desired current is by modification of the turns in the section of the magnet, as shown in FIG. 16B. Kinks in the conductor in the plates can be used. Kink 1660 produces a current similar to 1610, while kink 1670 produces a current perturbation similar to 1620; similar for the downstream section of the magnet. Thus, the quadrupole fields needed to minimize the transverse divergence of the beam can be directly integrated into magnet plates. These quadrupoles could be used to adjust for the focusing/defocusing discussed above (and illustrated in FIG. 14). However, one issue with this approach is that for fixed beam path, the quadrupole magnet is not "achromatic" when operated at fixed field, as charged particles of different energies would follow different paths in the magnet and thus, miss some of the quadrupole field, especially near the exit of the toroidal focusing magnet. One means to maintain fixed beam trajectory through the toroidal bending magnet so that the quadrupole fields remain effective, is to vary the field strength of the toroidal magnet as the beam energy is varied.

Figure 17:
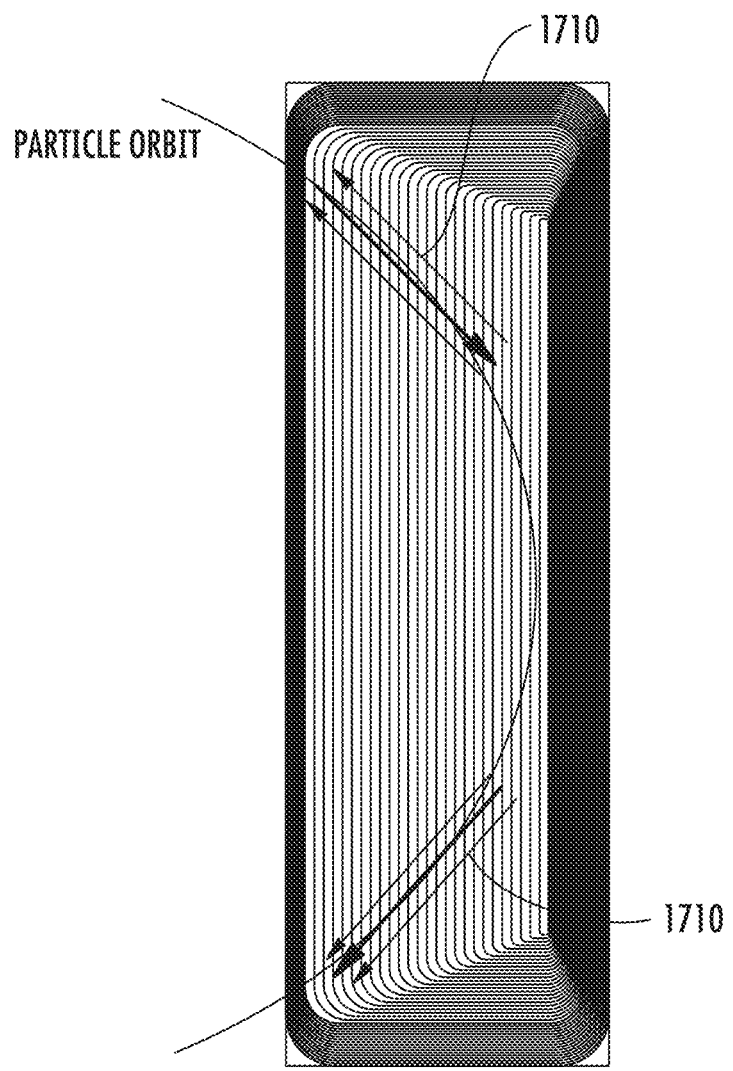
FIG. 17 shows a schematic of a different arrangement for modification of the current in the toroidal bending magnet that generates a quadrupole field in a different orientation than FIGS. 16A-16B.

FIGS. 16A-B illustrate how it is possible to make modifications to the turns in a pancake in order to create field modifications. The illustration involves making dipoles in each pancake that can be combined into quadrupoles. There are other ways to make dipoles, for example, having a main perturbation to the current, with two side-lines 1710 for the return current, each in a pancake, as shown illustratively in FIG. 17. As before, combining these modification generates a quadrupole. The configuration in FIG. 17 is better suited to controlling the azimuthal spreading of the beam, as it provides focusing/defocusing of the beam in the azimuthal direction. It is possible to have the orientation of the quadrupole in such a manner such that it provides focusing in azimuthal direction or in the plane of propagation of the beam. In addition, it is possible to generate quadrupole fields by having separate windings from those on the pancakes that generate the toroidal bending field. These windings can be on the same plane as the pancakes, and mounted on them, or they could be perpendicular to the pancakes, as saddle-like coils.

Figure 18:
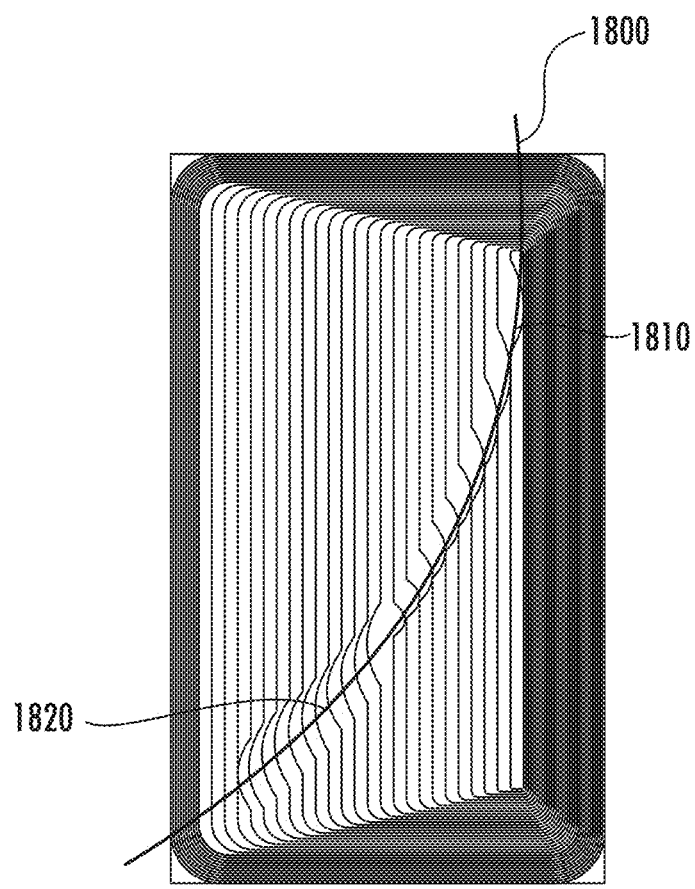
FIG. 18 shows axial beam injection, with quadrupole fields.

FIG. 18 shows a different implementation of the quadrupole pair, produced by modification of the current distribution in the plates of a constant-field toroidal magnet. In this case, the beam 1800 is introduced parallel to the major axis, near one end of the torus, and it exits through the periphery of the toroidal magnet, near the opposite end.

In the case shown in FIG. 18, two sets of quadrupole pairs 1810, 1820 are used, one near each end of the torus. Alternatively, conventional quadrupole magnets can be used. Note that as illustrated in the particle beam trajectories of the unmodified constant field magnet, there is a quadrupole field near the entrance/exit of the toroidal magnet.

Cooling Considerations

The superconducting bending magnets used on particle beam therapy gantries are generally cooled by conduction to a dedicated cold head, or cryogenerator. There are several reasons for this design choice. First, present gantry magnets are typically built using the low-temperature superconductor (LTS) NbTi. The liquefied helium gas needed to cool LTS magnets to their design operating temperature is becoming increasingly scarce and it is economically important to avoid loss of this expensive cryogen in case of off normal conditions. The release of vaporized cryogen boil-off is also not permitted in a clinical environment due to possible asphyxiation hazard. Second, due to the wide variation in gantry angle position about the patient treatment iso-center, it is difficult to guarantee uniform cooling by liquid cryogen bath in all possible gantry positions. Thirdly, conduction cooling by cryogenerator typically presents a lower system maintenance cost, requiring only annual servicing rather than weekly or monthly servicing needed for liquid helium cooled systems.

For in-depth beam scanning applications where the toroidal magnets are not used in achromatic pairs, the magnetic field in the magnets will need to be adjusted for each required beam energy. For swept field applications, it is important to minimize ac losses in the magnets and structure to the extent possible, to limit the required conduction cooling capacity. This consideration will help to minimize the required cryogenerator capacity.

At least three possible cooling schemes are envisioned for the gantry mounted toroidal bending magnets. The first scheme would be direct conduction to the cold head using high thermal conductivity metal plates also used as the magnet structure. To limit ac loss generation in these plates, they would need to be segmented using insulating breaks to minimize induced eddy currents during the field change. The second scheme would be to embed cooling pipes into the segmented magnet plates and to indirectly cool the magnet windings using a force flow of circulated helium cryogen gas. The third scheme would be to cool the magnet plates by residual gas conduction. This would be done by controlling the helium gas pressure within the cryostat (for example, to approximately 1 mTorr pressure) and introduce cooling fins into the gaps between magnet plates or in another structure. Cooling would occur by natural circulation of the residual helium gas between the magnet plates and the cooling fins, which would be cooled by conduction to the magnet system cold head.

In the case of indirect cooling, superconducting stability can be provided by placement of material with substantial heat capacity in the neighborhood of the superconductor, such as liquid helium or frozen hydrogen. The stabilizing material can be placed in a sealed environment, such that in the case of a quench, there is no release of large volume of gas. The sealed environment can be in the shape of sealed tubes (with the superconductor either inside or outside the tube), or it can be other sealed geometries, such as hollow glass spheres filled with helium, which would be added to the adhesive used to secure the conductors to the magnet plates.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A system for hadron therapies, comprising:
   a toroidal magnet, having a major axis passing through its center, comprising:
   a plurality of plates extending outward from the major axis, wherein each plate comprises a pancake coil disposed adjacent to a flat supporting element, wherein the pancake coil is configured so as to form a field-building region, a constant field region where a magnetic field varies by less than 25%, and a return current region; and
   a plurality of gaps, each gap disposed between a respective pair of adjacent plates; and
   a beam of charged particles directed toward one of the plurality of gaps in the toroidal magnet, wherein a path of the beam is planar with the major axis and the path forms an entry angle with the major axis which is greater than 0°, wherein the beam enters the gap from outside of the toroidal magnet, is directed along the path toward the major axis and is deflected away from the major axis and exits the gap at an exit angle equal to the entry angle.

2. The system of claim 1, wherein the plates are arranged symmetrically around the major axis.

3. The system of claim 1, wherein the plates are arranged in a plurality of bundles, and the plurality of bundles is arranged symmetrically around the major axis, wherein the gap between plates in a bundle is a different size than the gap between two plates in adjacent bundles.

4. The system of claim 3, wherein each bundle comprises two plates.

5. The system of claim 4, wherein the beam is directed toward a gap disposed between two plates in a bundle.

6. The system of claim 1, further comprising a quadrupole magnet to focus the beam.

7. The system of claim 6, wherein the quadrupole magnet is disposed upstream from the toroidal magnet.

8. The system of claim 6, wherein the quadrupole magnet is incorporated into the pancake coil.

9. The system of claim 1, wherein the toroidal magnet is constructed without ferromagnetic material.

10. The system of claim 1, wherein the flat supporting element comprises two opposite sides, and further comprising a second pancake coil disposed adjacent to the flat supporting element, such that a pancake coil is disposed on each of the two opposite sides of the flat supporting element.

11. The system of claim 1, wherein the charged particles comprise protons.

12. The system of claim 1, wherein a magnitude of a magnetic field in the toroidal magnet is selected such that the beam of charged particles does not extend into the gap past the constant field region.

13. A system for hadron therapies, comprising:
a first toroidal magnet, having a first major axis passing through its center, comprising:
  a plurality of first plates extending outward from the first major axis, wherein each first plate comprises a pancake coil disposed adjacent to a flat supporting element; and
  a plurality of first gaps, each first gap disposed between a respective pair of adjacent first plates;
a second toroidal magnet, having a second major axis passing through its center, comprising:
  a plurality of second plates extending outward from the second major axis, wherein each second plate comprises a pancake coil disposed adjacent to a flat supporting element; and
  a plurality of second gaps, each second gap disposed between a respective pair of adjacent second plates; and
a beam of charged particles directed toward one of the plurality of first gaps in the first toroidal magnet, wherein a path of the beam is planar with the first major axis and the path forms a first entry angle with the first major axis and exits the first toroidal magnet at a first exit angle relative to the first major axis; and
wherein the second toroidal magnet is configured such that the beam, after exiting the first toroidal magnet, is directed toward one of the second gaps at a second entry angle relative to the second major axis that is equal to the first exit angle from the first toroidal magnet.

14. The system of claim 13, wherein the pancake coils in the first toroidal magnet and the second toroidal magnet are configured so as to form a field-building region, a constant field region where a magnetic field varies by less than 25%, and a return current region.

15. The system of claim 1, where the toroidal magnet is self-shielding.

* * * * *